(12) United States Patent
Kaminski et al.

(10) Patent No.: US 11,346,839 B2
(45) Date of Patent: May 31, 2022

(54) METHOD FOR DETERMINING THE INTERACTION BETWEEN A LIGAND AND A RECEPTOR

(71) Applicant: INSINGULO AB, Mölndal (SE)

(72) Inventors: Tim Kaminski, Billdal (SE); Fredrik Höök, Alingsås (SE)

(73) Assignee: INSINGULO AB, Mölndal (SE)

( * ) Notice: Subject to any disclaimer, the term of this patent is extended or adjusted under 35 U.S.C. 154(b) by 0 days.

(21) Appl. No.: 17/263,582

(22) PCT Filed: Aug. 2, 2019

(86) PCT No.: PCT/EP2019/070925
§ 371 (c)(1),
(2) Date: Jan. 27, 2021

(87) PCT Pub. No.: WO2020/025808
PCT Pub. Date: Feb. 6, 2020

(65) Prior Publication Data
US 2021/0181193 A1     Jun. 17, 2021

(30) Foreign Application Priority Data

Aug. 3, 2018   (EP) .................................. 18187241

(51) Int. Cl.
*G01N 33/543*     (2006.01)
*G01N 21/64*      (2006.01)
*G01N 33/573*     (2006.01)

(52) U.S. Cl.
CPC ... *G01N 33/54373* (2013.01); *G01N 21/6452* (2013.01); *G01N 21/6458* (2013.01); *G01N 33/573* (2013.01); *G01N 21/648* (2013.01); *G01N 2333/974* (2013.01)

(58) Field of Classification Search
None
See application file for complete search history.

(56) References Cited

U.S. PATENT DOCUMENTS

2004/0047770 A1   3/2004  Schawaller et al.
2009/0041633 A1   2/2009  Dultz et al.
(Continued)

FOREIGN PATENT DOCUMENTS

CA          2 283 251      9/1998
WO    WO 2015/074931      5/2015

OTHER PUBLICATIONS

Geschwindner, Stefan, "Chapter 6: Label-Free Inhibition in Solution Assays for Fragment Screening" from Label-Free Biosensor Methods in Drug Discovery by Ye Fang, Methods in Pharmacology and Toxicology, Springer Science + Business Media New York, 2015, pp. 119-131. (Year: 2015).*

(Continued)

*Primary Examiner* — Bao-Thuy L Nguyen
*Assistant Examiner* — Xiaoyan Zou
(74) *Attorney, Agent, or Firm* — Ballard Spahr LLP (57) ABSTRACT

The disclosure concerns a method for determining the interaction between a test compound and a receptor. The receptor may be immobilized. The disclosure also concerns a sample holder assembly including a functionalized test well wall, which may be used in combination with a Total Internal Reflection Fluorescence source.

22 Claims, 4 Drawing Sheets

(56) References Cited

U.S. PATENT DOCUMENTS

2013/0050813 A1 2/2013 Kim et al.
2015/0362503 A1 12/2015 Korlach et al.

OTHER PUBLICATIONS

International Search Report and Written Opinion dated Dec. 4, 2020 by the International Searching Authority for International Application No. PCT/EP2019/070925, filed on Aug. 2, 2019 (Applicant—In Singulo Solutions AB) (16 Pages).

Geschwindner, Stefan. "Development of a Plate-Based Optical Biosensor Fragment Screening Methodology to Identify Phosphodiesterase 10A Inhibitors", Journal of Medicinal Chemistry (2013) 56, pp. 3228-3234.

Gunnarsson, Anders et al. "Drug Discovery at the Single Molecule Level: Inhibition-in-Solution Assay of Membrane-Reconstituted β-Secretase Using Single-Molecule Imaging", Analytical Chemistry (2015), 87, pp. 4100-4103.

Gunnarsson, Anders et al., "Kinetics of Ligand Binding to Membrane Receptors from Equilibrium Fluctuation Analysis of Single Binding Events", Journal of the American Chemical Society (2011), 133, pp. 14852-14855.

Johansson, Maja et al. "GR3027 reversal of neurosteroid-induced, GABA—A receptor-mediated inhibition of human brain function: an allopregnanolone challenge study", Psychopharmacology (2018), 235, pp. 1533-1543.

Kaminski, Tim et al. "Perspectives on optical biosensor utility in small-molecule screening", Expert Opinion on Drug Discovery (2017), vol. 12, No. 11, pp. 1083-1086.

Motulsky, Harvey J. et al. "The Kinetics of Competitive Radioligand Binding Predicted by the Law of Mass Action", Molecular Pharmacology (1983) 25, pp. 1-9.

Schiele, Felix et al. "A universal homogenous assay for high-throughput determination of binding kinetics", Analytical Biochemistry 468 (2015), pp. 42-45.

Wahlsten, Olov et al. "Equilibrium-Fluctuation Analysis for Interaction Studies between Natural Ligands and Single G Protein-Coupled Receptors in Native Lipid Vesicles", Langmuir (2015) 31, pp. 10774-10780.

International Preliminary Report on Patentability dated Nov. 11, 2020 by the International Preliminary Examining Authority for International Application No. PCT/EP2019/070925, filed on Aug. 2, 2019 (Applicant—In Singulo Solutions AB) (17 Pages).

* cited by examiner

METHOD FOR DETERMINING THE INTERACTION BETWEEN A LIGAND AND A RECEPTOR

CROSS-REFERENCE TO RELATED APPLICATIONS

This application is a U.S. National Phase Application of International Application No. PCT/EP2019/070925, filed Aug. 2, 2019, which claims priority to European Patent Application No. 18187241.7, filed Aug. 3, 2018, each of which are hereby incorporated by reference in its entirety.

TECHNICAL FIELD

The present disclosure relates to a method for determining the interaction between a first ligand such as a test compound and a receptor such as a target molecule. The present disclosure also relates to a sample holder assembly for use in said method.

BACKGROUND

Biosensors are used in drug discovery for the generation of binding kinetic data, which can be used to further the understanding of structure-kinetic relationships during the compound optimization process. Kinetic information is frequently deduced through microfluidics-based biosensor platforms like surface plasmon resonance (SPR), as the optimized fluidics and the high sampling rates allow for an exact description of molecular association and dissociation processes. Information about extended dissociation processes can eventually provide possibilities to enhance compound efficacy and safety and thus may help to ensure therapeutic success if correlated with the corresponding pharmacokinetic features.

All optical biosensor platforms follow the same guiding principle by attaching one interaction partner, usually the drug target protein, oligonucleotide or even entire cells, to a biosensor surface. The modified surface is subsequently challenged with solutions containing test compounds in order to obtain direct binding information or to study the biological consequences of binding when working with cellular systems. This assay configuration is called a direct binding assay (DBA).

Surface plasmon resonance (SPR) and optical waveguide (OWG) make use of an evanescent-wave phenomenon and thus are able to measure changes in the refractive index that are proportional to changes in molecular mass at the sensor surface. In contrast, bio layer interferometry (BLI) operates through the analysis of interference patterns that enables to monitor changes in the effective optical thickness of the layer that is in direct contact with the sensor. Common for all platforms is the capability for time resolved measurements of the binding interaction, particularly when using microfluidics-based systems. As optical biosensor systems do not require any labelling of the used reagents, they are often referred to as label-free technologies aiming to reduce the number of assay artefacts that may possibly be introduced by labelling either the target or the compound.

One common property of microfluidic based biosensor platforms is the need for two separate experiments. First, the sensor surface is brought into contact with the analyte. Thereby, a reaction, the rate of which being, in the simplest case, a convolution of the association, $k_{on}$, and dissociation, $k_{off}$, rate constants, is measured. Typically, this reaction is observed until equilibrium coverage on the sensor surface is reached, the coverage of which being determined by the equilibrium dissociation constant, $K_d = k_{off}/k_{on}$. Subsequently, the sensor surface is exposed to an analyte-free solution with the intention to monitor the dissociation reaction alone, from which $k_{off}$ can be directly deduced.

This type of biosensing comes with a number of drawbacks, especially if the target molecule is a membrane protein. It has been estimated that about 60% of all approved drug targets are membrane proteins. Especially for membrane proteins the success rate is low ~30%.

Many drug targets, especially membrane proteins are incompatible with the immobilization at the sensor surface. Therefore, time and resource intensive modifications has to be introduced to the target.

They require a high density of the drug target at the surface since the signal amplitude is proportional to the number of immobilized targets.

These systems are only capable of detecting net changes at the surface. They are therefore blind to the binding and unbinding dynamics at equilibrium.

These sensor platforms offer very limited number of sensor surfaces. SPR system usually have 3-4 separate sensor surfaces. That means that if the target becomes dysfunctional, the sensor is "lost". Next to the sensor cost the device cannot record any further data for that particular surface. This limits the throughput dramatically.

Before a new run can be started, the sensor surface has to be free of any test compound. For long residence time compounds this can be challenging and surface regeneration is often limiting the throughput.

The sensitivity is limited by technical features of the biosensor platform.

One way to mitigate the problem of target immobilization is to keep the drug target in solution. Instead of immobilizing the target a so-called tool-compound is immobilized, with which the suspended target is known to interact with in a specific manner. The test compound is added to the target outside the instrument to allow target molecules and test compound molecules to react, and the resulting solution is thereafter injected over the immobilized tool compound. This technology is commonly referred to as Inhibition in Solution Assay (ISA). Hence, by investigating how different concentrations of a test compound influences the binding of the target to the tool compound, one can determine the equilibrium dissociation constant, $K_d$, of the test compound to the drug target. J. Med. Chem., (2013), 56, 3228-3234 discloses this type of assay. For conventional label-free technologies, the immobilized tool-compound has to dissociate from the drug target slowly. Obtaining such a tool-compound is challenging.

In contrast to DBAs, the configuration of label-free technologies does not enable measurements of binding kinetics in combination with an ISA, i.e. the association rate constant $k_{on}$ and the dissociation rate constant $k_{off}$. Mol. Pharmacol. (1984), 25, 1-9 discloses that non-label free technologies allow to measure kinetics in a very limited range by competition experiments, and also describes mathematically how the binding kinetics is changed if two ligands are competing for binding to the target. If the kinetics of one of the ligands is known (ligand A) and this ligand is labelled which makes it possible to distinguish it from the other ligand (ligand B)—the binding kinetics of ligand B can be determined by recording the binding kinetics of ligand A. Anal. Biochem. (2015), 468, 42-49 discloses that these assays need a labelled tool-compound that binds the target with high affinity.

Anal. Chem. (2015), 87, 4100-4103 discloses a single-molecule based ISA (SMM-ISA) that allows to perform inhibition in solutions assays with high sensitivity. For this method the target is not immobilized at the surface but is instead immobilized in/at a suspended freely diffusing liposome that carry fluorescent dyes in its lipid environment. On the surface a tool-compound that can bind to the target is immobilized. The modified surface is imaged with a total internal reflection fluorescence (TIRF) microscope. TIRF generates an evanescent field of excitation light which will only excite liposomes that are close to the surface (couple of 100 nm). By keeping the concentration of liposomes low, single-liposomes binding to and dissociating from the surface can be imaged. In contrast to the conventional methods described above, the high sensitivity of the single-molecule assay allows the affinity of the tool-compound to the drug target to be orders of magnitude lower. In addition, the concentration of the target-containing liposome can be orders of magnitude lower than in conventional ISA.

However, in the first reports on SMM-ISA it was only the binding kinetics between the target and the surface-immobilized tool compound that could be determined, and not the dynamic kinetic parameters (the association, $k_{on}$, and the dissociation, $k_{off}$, rate constants) of the crucial interaction between the target and the test compounds. An additional drawback was the low throughput and high amount of manual work that had to be done. This limits cost efficiency, reproducibility and thus reliability, therefore not fulfilling industry requirements.

Langmuir, 2015, 31 (39), pp 10774-10780 discloses use of total internal reflection fluorescence microscopy to characterize the kinetics between CXCR3, a GPCR involved in inflammatory responses, and two of its chemokine ligands, CXCL10 and CXCL11. Fluorescence labeling of the lipid membrane, rather than the membrane protein itself, of GPCR-containing containing native vesicles, and immobilization of the corresponding ligand on the surface, enabled the determination of the dissociation constant between the receptor and the ligand in solution using single-molecule equilibrium-fluctuation analysis. The interaction between the CXCR3 and the chemokine ligands CXCL10 and CXCL11 was made under stagnant liquid conditions.

J. Am. Chem. Soc., 2011, 133, 14852-14855 discloses kinetics of ligand binding to membrane receptors from equilibrium fluctuation analysis of single binding events. Stagnant liquid conditions were used and each association and dissociation event was monitored over time by TIRF microscopy in a microwell format.

It is an object of the present disclosure to overcome or at least mitigate some of the problems described above. Further, an object of the present disclosure is to provide advantages and/or aspects not provided by hitherto known technique.

SUMMARY

The present disclosure provides a method for determining the interaction between a first ligand and a receptor,
said method comprising a sequence of process steps:
a) providing a first solution free from the first ligand and comprising a concentration $C_i$ of the receptor,
b) contacting said first solution with a test well wall functionalized with a second ligand while recording the number of binding events between the receptor and the second ligand during a time interval $t_1$, and
c) adding a test solution free from said receptor and comprising a concentration $C_n$ of the first ligand to the first solution thereby providing a second solution while continuing recording the number of binding events between the second ligand and the receptor in said second solution during a time interval $t_2$.

Importantly, the recording of the number of binding events in the method described herein takes place during the addition of the test solution comprising the first ligand, i.e. step c) and may be started shortly after the addition of the first ligand before the second solution reaches equilibrium. This is in contrast to stagnant conditions where the recording of the binding events takes place only after the addition of the first ligand and the binding between the first ligand and the receptor has reached equilibrium or quasi-equilibrium. Thus, the method described herein uses non-stagnant conditions such as non-stagnant liquid conditions. As a result, the determination of the interaction between the first ligand and the receptor is made prior to equilibrium binding between said first ligand and said receptor. It is a significant advantage of the method described herein that it does not require waiting for the first ligand and the receptor to reach or substantially reach equilibrium which makes the total time for making the measurement longer. Instead, the method described herein allows for a fast throughput when measurements are performed. Of course, this is particularly advantageous in screening applications.

It will be appreciated that the recording of binding events in step b) is optional. In an example, the recording of binding events in step b) does not take place or takes place prior to, such as just prior to, step c). Thus, there is provided a method as described herein wherein step b) is:

b) contacting said first solution with a test well wall functionalized with a second ligand while the number of binding events between the receptor and the second ligand during a time interval $t_1$ is recorded or is not recorded.

A further advantage of the method described herein is that the binding kinetics between the second ligand and the receptor do not have to be known or determined.

The time interval $t_2$ is at least $1/k_{obs}$ of the binding reaction between the first ligand and the receptor. Thus, the time interval $t_2$ may be equal to or above $1/k_{obs}$ of the binding reaction between the first ligand and the receptor. $k_{obs}$ may be measured and calculated as described herein.

In an example, the recording of the binding events between the second ligand and the receptor takes place until the first ligand and the receptor have reached equilibrium binding. In a further example, the recording of the binding events between the second ligand and the receptor takes place until and after the first ligand and the receptor have reached equilibrium binding.

It will be appreciated that the method described herein may be performed in such a way that the recording of the binding events between the receptor and the second ligand is not interrupted between steps b) and c), i.e. the recording takes place in a continuous manner. Further, the time interval $t_1$ intends the time range from adding the receptor in step b) until the first ligand is added in step c). Moreover, the time interval $t_2$ intends the time range from adding the first ligand in the test solution in step c) until at least the first ligand and the receptor have reached equilibrium binding as described herein or is at least $1/k_{obs}$.

The equilibrium binding described herein may be binding at quasi-equilibrium, i.e. near equilibrium or substantially at equilibrium.

The method described herein may further comprise a step d):

d) determining the interaction between the first ligand and the receptor based on the binding events recorded in steps b) and c).

In this document, the first ligand may be a test compound. The terms "first ligand" and "test compound" may be used interchangeably. Further, in this document the term "receptor" may be a target such as a drug target. The terms "receptor" and "target" may be used interchangeably. Moreover, in this document the second ligand may be a tool compound. The terms "second ligand" and "tool compound" may be used interchangeably.

The sequence of process steps of the method described herein may be performed in full in each of a plurality of test wells.

Each method step may be carried out at the same time in each test well, i.e. the first step may be carried out at the same time in each test well and then each consecutive step may be carried out at the same time in each test well. Alternatively, the method steps may be carried out at different times in the test wells.

The number of receptors binding to the test wall may be recorded before and after the addition of the first ligand. These recorded binding events may be summed up for the plurality of test wells. The number of binding events before addition of the first ligand may be recorded during a time interval $t_1$ as described herein. The number of binding events after addition of the first ligand may be recorded during a time interval $t_2$ as described herein. The time intervals $t_1$ and $t_2$, respectively, may be the same or different. The summed up recorded binding events before the addition of the test compound, and the summed up recorded binding events after the addition of the test compound, respectively, may subsequently be used for determining the interaction between the first ligand and the receptor. When the method steps are not carried out at the same time in each test well this has to be taken into consideration to make a correct summing up the binding events in the plurality of test wells.

Further, the sequence of process steps may be performed for a number of different concentrations $C_n$ of the first ligand in said test solution. Accordingly, the method described herein may comprise a step e):

e) repeating step c) at an increasing concentration $C_n$ of the first ligand in said test solution.

Importantly, the test solution of the method described herein is free from receptor and is added to the first solution. Thus, the first ligand and the receptor are not allowed to react prior to adding the test solution to the first solution. These features distinguish the method described herein from Inhibition in Solution Assays (ISA) where the test solution comprises both a receptor and a test compound which are allowed to react prior to being added to a functionalized surface.

The test well wall described herein may be a test well bottom wall of a single test well or a plurality of test wells. The test well wall is functionalized with a second ligand which faces the interior of the test wells whereby the second ligand is immobilized. The functionalization of the test well wall may take place using techniques known in the art. For instance, the test well wall may be treated with a piranha solution followed by functionalization of the test well wall.

The receptor may be used as such or used in combination with a vehicle. The receptor and/or the vehicle may be labelled or unlabelled. The labelling may include a fluorophore.

In an example, there is provided a vehicle comprising a fluorophore. The combination of the receptor with a vehicle allows for immobilizing said receptor without or substantially without negatively impacting the receptor structure. Additionally, the vehicle can provide the receptor an environment representing or mimicking its native environment, especially if it is a membrane receptor. The immobilized receptor may be soluble or substantially soluble in a selected solvent or the vehicle or a combination of the vehicle and the solvent.

Examples of vehicles that may be used for immobilizing the receptor include, but are not limited to, at least one of the following: a liposome, a liposome, a dendrimer, a dendrone, a complexed lanthanide, a quantum dot, a nanodiamond, a lipid disc.

The first ligand and the second ligand may be the same or different. Thus, in contrast to methods requiring the dissociation rate of the receptor from the surface bound second ligand to be known or measured the first and second ligand may be different from each other.

The receptor may be a pharmaceutical drug receptor. For instance, the receptor may comprise or consist of thrombin. Additionally or alternatively, the first ligand and/or the second ligand may be a pharmaceutical drug. For instance, the pharmaceutical drug may be melagatran.

The steps b) and/or c) of the method described herein may comprise use of a microscope. Frequently, the use of a microscope is appropriate for recording the number of binding events between the receptor and the second ligand. Examples of suitable techniques that may be used in conjunction with the method of the present disclosure include image analysis, Surface Plasmon Resonance (SPR), Total Internal Reflection Fluorescence (TIRF), waveguide imaging, interferometric scattering, light field microscopy, epi fluorescence microscopy, laser scanning microscopy, orbital scanning microscopy, local enhancement microscopy, structured illumination microscopy, RESOLFT microscopy, spatially modulated illumination, omnipresent localization microscopy, and/or x-ray microscopy.

The method described herein may allow for and/or comprise determination for the first ligand at least one of, i.e. one or more of, the following: an observed rate constant $k_{obs}$, an association rate constant $k_{on}$, a dissociation rate constant $k_{off}$, an equilibrium dissociation constant $K_d$, a fractional occupancy.

The rate constant $k_{obs}$ characterizes how fast the receptor becomes occupied with the first ligand. It depends on the association rate constant $k_{on}$, the dissociation rate $k_{off}$ and the concentration $C_n$ of the test compound as shown in equation 1.

$$k_{obs} = k_{on}C_n + k_{off} \quad \text{Equation 1:}$$

The receptor bound by the first ligand cannot bind not anymore to the second ligand or binds differently to the immobilized second ligand. The number of binding events per unit time is denominated $\alpha(t)$ and is given by equation 2 below.

$$\alpha(t) = k_{on,V} C_{i,free}(t<t_{inh}) \quad \text{Equation 2:}$$

It will be appreciated that $C_{i,free}(t<t_{inh})$ is the concentration of receptor not bound by the first ligand or the immobilized second ligand at a time t which is less than the time at which the first ligand (inhibitor) is added, i.e., $t_{inh}$. Further, $k_{on,V}$ is the association rate constant for the first ligand to the receptor, said receptor binding to a vehicle such as a vehicle.

Upon the addition of said first ligand with concentration $C_n$, $C_{i,free}$ (t<$t_{inh}$) changes into $C_{i,free}(t)$ as shown in equation 3 below.

$$C_{i,free}(t)=C_{i,free}(t<t_{inh})(1-\beta(t))\qquad\text{Equation 3:}$$

In equations 3 and 4, β (t) represents the fraction of receptors in complex with the first ligand at a time t. β (t) may have a value between 0 and 1, i.e. 0<β(t)<1. β(t) may be determined as shown in equation 4 below.

$$\beta(t)=C_n/(C_n+K_d)*[1-\exp(-k_{obs}*(t-t_{inh}))]\qquad\text{Equation 4:}$$

As described herein, $C_n$ is the concentration of the first ligand, $K_d$ is the equilibrium constant, $k_{obs}$ is the observed rate constant, t is the time at which the measurement is made and $t_{inh}$ is the time at which the first ligand (inhibitor) is added.

The equilibrium dissociation constant $K_d$ for the first ligand is described in Equation 5, where [L] is the concentration of the first ligand, [R] is the concentration of the receptor and [LR] is the concentration of the receptor binding to the test compound.

$$K_d = \frac{[L][R]}{[LR]} \qquad\text{Equation 5}$$

$K_d$ may also be expressed as the ratio between the dissociation constant $k_{off}$ and the association constant $k_{on}$ as shown in equation 6.

$$K_d=k_{off}/k_{on}\qquad\text{Equation 6:}$$

The fractional occupancy is the amount of receptor-ligand complex divided by the initial amount of receptor as shown in Equation 7, where [Ligand Receptor] is the concentration of the first ligand binding to the receptor at equilibrium and [Total receptor] is the initial concentration of the receptor.

$$\text{Fractional occupancy} = \frac{[\text{Ligand Receptor}]}{[\text{Total Receptor}]} \qquad\text{Equation 7}$$

The fractional occupancy may also be expressed as indicated in Equation 8, where [Ligand] is the concentration of free first ligand at equilibrium of the binding reaction and $K_d$ is as described herein.

$$\text{Fractional occupancy} = \frac{[\text{Ligand}]}{[\text{Ligand}] + K_d} \qquad\text{Equation 8}$$

When the method of the present invention is performed in a plurality of test wells these may form part of a sample holder assembly such as a microtiter plate. Thus, the sample holder assembly may comprise or consist of a microtiter plate. Such sample holder assemblies allow for performing a large number of experiments in a time-and cost efficient way. Further, performing the method in a plurality of test wells allows for increasing the sensitivity since the number of recorded binding events in the test wells may be summed up thereby providing more data points.

Advantageously, the use of a plurality of test wells as described herein allows for avoiding so-called ligand depletion which may occur when there are too many receptor binding spots for too few ligands so that the ligands become depleted. In order to avoid ligand depletion the receptor concentration should be lowered. However, this leads to poor signal strength since the signal strength in binding assays is usually proportional to the concentration of the receptor. The use of a plurality of test wells in the method described herein compensates for poor signal strength by allowing for summing up data points from several test wells.

It has been found that TIRF is a suitable technique to be used in conjunction with the method described herein. Accordingly, there is provided a method as described herein wherein the sample holder assembly is configured to be used in combination with Total Internal Reflection Fluorescence (TIRF) microscopy and comprises:
 a sample holder plate comprising a plurality of bottomless test wells
 a bottom plate attached to said sample holder plate by means of a material such as an attachment means such as an adhesive thereby forming a well bottom wall of said plurality of test wells,
said material such as attachment means such as adhesive having a refractive index $N_a$ that is lower than a refractive index $N_g$ of said bottom plate.

Traditionally, the TIRF source is provided from below the bottom plate of the sample holder assembly. This would be time consuming for a plurality of wells since the TIRF source then would have to be moved around. Instead, the TIRF source may be placed so that the light beam is propagated throughout the entire bottom plate. However, this also requires that the light beam does not leak into e.g. the test well bottom wall. Additionally, the attachment means such as an adhesive should be able to attach reliably and fast to the walls of the sample holder assembly when put together and also withstand chemicals such as solutions and reagents added to the sample holder wells.

For instance, the attachment means may be an adhesive. Advantageously, the adhesive described herein may be UV curable and/or resistant to buffer solutions. The UV curability allows for convenient and fast attachment of the functionalized test well wall to the walls of the sample holder plate. The resistance to buffer solutions prevents the functionalized test well wall from being detached from the sample holder plate.

The adhesive may comprise a silane from at least one of the following: alkylsilanes, aminosilanes, epoxysilanes, hydrosils, mercaptosilanes, methacrylic silanes.

In order to allow for the light beam from the TIRF source to propagate throughout the entire bottom plate without being leaked into adjacent media such as the sample holder bottom plate the adhesive should be selected to have a refractive index $N_a$ that is lower than a refractive index $N_g$ of said bottom plate. In this way, an evanescent wave will be created closely to an inner surface of the functionalized test well wall. Fluorescent receptors or fluorescent vehicles immobilizing the receptor, i.e. fluorophores, will then become excited and fluoresce in proximity of the said surface. In this way, the measured fluorescence will originate only from the fluorophore in proximity of the surface while fluorophores further away from the surface will not fluoresce.

Accordingly, the present disclosure provides a method as described herein, wherein the sample holder assembly is combined with a TIRF source configured to provide a light beam into the well bottom wall such that the light beam propagates throughout the entire well bottom wall thereby creating an evanescent field in the plurality of wells.

The sample holder assembly may be prepared in advance to suit an intended application. For instance, the sample holder assembly bottom plate may be prepared by surface modification for a particular application and then attached to the remainder of the sample holder assembly with the aid of the attachment means described herein.

Further, the present disclosure provides a use of a method as described herein for evaluating the binding kinetics between two or more different first ligands and a receptor without varying the second ligand.

The present disclosure also provides a sample holder assembly configured to be used in combination with TIRF microscopy, comprising:
a sample holder plate comprising a plurality of bottomless test wells,
a bottom plate attached to said sample holder plate by means of a material such as an attachment means such as an adhesive thereby forming a well bottom wall of said plurality of test wells,
said adhesive having a refractive index $N_a$ that is lower than a refractive index $N_g$ of said bottom glass plate (3). The material such as an attachment means such as an adhesive may be UV curable and/or resistant to buffer solutions. The sample holder plate may comprise or consist of a microtiter plate.

The sample holder assembly disclosed herein may be combined with a TIRF source configured to provide a light beam into the well bottom wall such that the light beam propagates throughout the entire well bottom wall thereby creating an evanescent field in the plurality of wells.

DETAILED DESCRIPTION OF PREFERRED EMBODIMENTS

Figure 7:
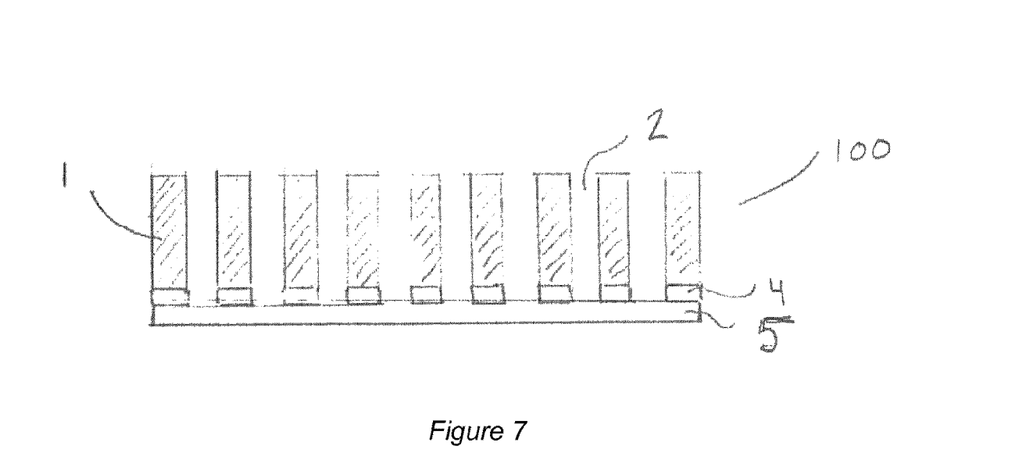
FIG. 7 is a cross section view of a microtiter plate comprising a plurality of test wells comprising a functionalized bottom plate attached to said microtiter plate by means of an adhesive.

FIG. 7 shows a cross section of a sample holder assembly 100 comprising a sample holder plate 1 comprising a plurality of bottomless test wells 2, a bottom plate 3 attached to the sample holder plate 1 by means of an adhesive 4 thereby forming a well bottom wall 5 of said plurality of wells 2. The adhesive has a refractive index $N_a$ that is lower than the refractive index $N_g$ of said bottom plate 3.

As explained herein, the adhesive 4 may be elected to allow for a TIRF light beam to propagate throughout the entire bottom plate without leaking into adjacent media such as the bottom plate. Thereby an evanescent wave is created closely to the bottom plate which may be used in the detection of binding events as described herein.

The well bottom wall 5 may be functionalized with a tool compound as described herein.

Further Items

The present disclosure provides the following items.

Item 1:
A method for determining the interaction between a first ligand and a receptor, said method comprising a sequence of process steps:
a) providing a first solution free from said first ligand and comprising a concentration $C_i$ of the receptor,
b) contacting said first solution with a test well wall functionalized with a second ligand while recording the number of binding events between the receptor and the second ligand during a time interval $t_1$,
c) adding a test solution free from said receptor and comprising a concentration $C_n$ of the first ligand to said first solution thereby providing a second solution while recording the number of binding events between the second ligand and the receptor of said second solution during a time interval $t_2$.

Item 2:
A method according to item 1, wherein the sequence of process steps is performed in full in each of a plurality of test wells.

Item 3:
A method according to item 1 or 2, wherein the sequence of process steps is performed for a number of different concentrations $C_n$ of the first ligand in said test solution.

Item 4:
A method according to item 1 or 2 further comprising a step d):
d) repeating step c) at an increasing concentration $C_n$ of the first ligand in said test solution.

Item 5:
A method according to any one of the preceding items, wherein
the receptor is combined with a vehicle such as a liposome, a dendrimer, a dendrone, a complexed lanthanide, a quantum dot, a nanodiamond or a lipid disc,
thereby providing an immobilized receptor.

Item 6:
A method according to any one of the preceding items, wherein the vehicle comprises a fluorophore.

Item 7:
A method according to any one of the preceding items, wherein the first ligand and the second ligand are the same or different.

Item 8:
A method according to any one of the preceding items, wherein:
the receptor is a pharmaceutical drug receptor, and/or
the first ligand and/or the second ligand is/are a pharmaceutical drug.

Item 9:
A method according to any one of the preceding items, wherein step b) and/or step c) comprise(s) use of a microscope.

Item 10:
A method according to any one of the preceding items, which comprises determination for the first ligand at least one of the following: an observed rate constant $k_{obs}$, an association constant $k_{on}$, a dissociation constant $k_{off}$, an equilibrium dissociation constant $K_d$, a fractional occupancy Item 11:
A method according to any one of items 2-10, wherein the plurality of test wells form part of a sample holder assembly such as a microtiter plate.

Item 12:
A method according to item 11, wherein the sample holder assembly is configured to be used in combination with Total Internal Reflection Fluorescence (TIRF) microscopy, and comprises:
  a sample holder plate (1) comprising a plurality of bottomless test wells (2),
  a bottom plate (3) attached to said sample holder plate (1) by means of an adhesive (4) thereby forming a well bottom wall (5) of said plurality of wells (2),
said adhesive (4) having a refractive index ($N_a$) that is lower than a refractive index ($N_g$) of said bottom plate (3).

Item 13:
A method according to any one of items 10-12, wherein said adhesive (4) is UV curable and/or resistant to buffer solutions.

Item 14:
A sample holder assembly (10) configured to be used in combination with TIRF microscopy, comprising:
  a sample holder plate (1) comprising a plurality of bottomless test wells (2),
  a bottom plate (3) attached to said sample holder plate (1) by means of an adhesive (4) thereby forming a well bottom wall (5) of said plurality of wells (2),
said adhesive (4) having a refractive index ($N_a$) that is lower than a refractive index ($N_g$) of said bottom glass plate (3).

Item 15:
A method according to item 11 or a sample holder assembly (10) according to claim 14, wherein the sample holder assembly (10) is combined with a TIRF source configured to provide a light beam into the well bottom wall (5) such that the light beam propagates throughout the entire well bottom wall (5) thereby creating an evanescent field in the plurality of wells (2).

EXAMPLES

Abbreviations
CHES N-Cyclohexyl-2-aminoethanesulfonic acid
HBS Hepes buffered solution
HEPES (4-(2-hydroxyethyl)-1-piperazineethanesulfonic acid)
LED Light Emitting Diode
NHS N-Hydroxysuccinimid
μl microliter
L liter
LOD lower limit of detection
nm nanometer
nM nanoMolar
mg milligram(s)
ml milliliter
mM millimolar
PBS Phosphate buffered solutions
PEG4 Polyethylene glycol, i.e. H—(O—CH$_2$—CH$_2$)$_4$—OH.
PC Phosphatidylcholine
PEG polyethylene glycol
PLL-g-PEG poly-L-lysine grafted PEG
RT room temperature
sec second(s)
UV ultraviolet
V/V volume percent Materials and Methods
All lipids were bought from Avanti Polar Lipids.
Pll-g-PEG (11354-X=200-2000-3.5%) and PLL-g-PEG-biotin (11835-X=200-3400-3.5%) were bought from Nanosoft Polymers.
The thrombin binding peptide was synthezised upon customer specification by ThermoFisher Scientific. Melagatran was purchased from SantaCruz Biotechnology.
Dymax 3025 is a product of Dymax Corporation.
All other chemicals if not stated differently were bought from Sigma. All chemicals were suitable for molecular biology purposes.

Preparation of Liposomes:
To yield liposomes with a diameter of ~100 nm first the required lipids were solved in chloroform and mixed. In total 5 mg 2-Oleoyl-1-palmitoyl-sn-glycero-3-phosphocholine, 0.01 mg, 1,2-dioleoyl-sn-glycero-3-phosphoethanolamine-N-dibenzocyclooctyl and 0.005 mg 1,2-dipalmitoyl-sn-glycero-3-phosphoethanolamine-N-(lissamine rhodamine B sulfonyl) were mixed together. The lipid mixture was vacuum dried overnight. The dried lipids were hydrated in 1 ml HBS (150 mM NaCl, 20 mM/L HEPES at pH7.2) under gentle agitation. The lipid suspension was extruded through a PC-membrane with 100 nm pore size eleven times. Concentration of the liposomes was determined by light absorption at 544 nm and the concentration of the liposome solution was adjusted to 2.5 mg/ml. This equals a liposome concentration of approximately 30 nM.

Preparation of Protein:
To immobilize thrombin at the liposomes via click chemistry an azide-group was introduced to thrombin via NHS coupling. Therefore, 100 μL of human-thrombin at 2 mg/ml was mixed with 200 μL high salt PBS-buffer (10 mM Na$_2$HPO$_4$, 1.8 mM KH$_2$PO$_4$, 400 mM NaCl+33.5% Glycerol (v/v) at pH 7.4 and 13 μL NHS-PEG4-Azide at 10 mM. The mixture was incubated for 30 minutes at RT. The reaction was stopped by the addition of 500 μL high salt PBS-buffer (10 mM Na$_2$HPO$_4$, 1.8 mM KH$_2$PO$_4$, 400 mM NaCl+33.5% Glycerol (v/v) at pH 6.6.

Immobilization of Protein:
1.5 μL of the thrombin-azide were mixed with 48.5 μL icecold CHES-buffer (20 mM CHES, 150 mM NaCl) at pH 8.5 and subsequently 50 μL of the liposome solution is added. This mix was stored for at least 30 minutes on ice. 10 μL of the reaction mix was diluted with 990 μL icecold CHES-buffer (20 mM CHES, 150 mM NaCl) at pH 8.5.

Preparation of Surfaces:
A glass plate with 0.17 mm thickness was incubated in base piranha solution at 373 Kelvin for 30 minutes. The cleaned glass plate was rinsed with water and dried. An UV curable adhesive (Dymax 3025) was supplemented with ~1% (v/v) (3-Aminopropyl)-triethoxysilane. The adhesive mixture was thinly spread at the lower side of the bottomless microplate. The glass plate was positioned on top of the bottomless microplate so it formed the bottom. After the adhesive was spread fully, it was cured according to manufacturer instructions. After curing, into each well of the microplate 10 μL of a solution containing 1 mg/ml PLL-g-PEG and 1 mg/ml PLL-g-PEG-biotin are added. The plate was incubated for at least 1 h under gentle orbital agitation. After the incubation each well was washed 10-times with HBS-buffer. The dilution ratio of every washing step was at least 1:10. After washing, into each well 10 μL of a solution containing 100 μg/mL neutravidin was added. This was incubated for at least 4 h under gentle orbital agitation. All wells were washed as previously described and 10 μL of a solution containing 10 ug/ml a thrombin binding peptide linked to biotin (GVGPRSFKLPGLA-Aib-SGFK-PEG$_4$-biotin) was added to all wells. The microplate was incubated at least for 1 h under gentle orbital agitation. The peptide was the tool compound to bind the thrombin immobilized at the vesicles.

Finally the microplate was washed as previously described and the residual buffer volume in each well is 30 µL.

The Microscope Setup:

The single molecule microscope was based on a Nikon Ti-E base. As light source for epifluorescence a LED-white light source is used. The Objective was a 60×APO TIRF objective. Images are recorded via a HAMAMATSU Orca-FLASH 4.0V2 sCMOS camera. The sample stage was motorized and quipped with a microwell holder.

On top of the microscope liquid handling robotics were installed (Andrew, Andrew Alliance).

Melagatran Dilution Series:

An 8 times 1:3 dilution series of melagatran starting at 1.6 uM/L. The buffer for the dilution series was CHES-buffer (20 mM CHES, 150 mM NaCl) at pH 9.5.

Example 1

The microwell plate comprising 384 wells was placed in the microwell plate holder at the microscope. Subsequently the measurement was started and conducted fully automatically.

The single molecule measurement included the following steps in each well:
1. The appropriate microwell prepared as indicated above was placed over the objective and the objective was adjusted so its focal plane is placed at the inner surface of microwell.
2. The well was washed with 70 µL CHES-buffer (20 mM/L CHES, 150 mM/L NaCl) at pH 9.5.
3. 5 µL of a solution containing CHES buffer and the liposome onto which thrombin was attached was added to the well and the well content mixed.
4. The acquisition of time lapse movie with 901 images and an acquisition rate of 10 sec$^{-1}$ was started
5. After 20 seconds of acquisition 5 µL solution containing the appropriate concentration of melagatran and CHES buffer was added and the well content mixed rapidly (<0.5 sec).
6. The acquisition of image data was continued till 901 frames were recorded.

Steps 1-6 were repeated three times for each intended concentration of melagatran. Eight concentrations of melagatran were tested, namely 200 nM, 66.7 nM, 22.2 nM, 7.4 nM, 2.5 nM, 0.8 nM 0.3 nM and 0.1 nM. For each tested concentration of melagatran steps 1-6 above were performed in full in each well. Each method step was carried out at the same time in each well, i.e. step 1 was carried out at the same time in each well and then each consecutive step was carried out at the same time in each well.

The recorded image data was analysed with the aim to determine the number of new bound liposome in each well. In a first step all objects that are similar in shape to a reference object in each well were detected.

In a second step it was determined which objects were bound to the surface. As indication that an object was bound to the surface its mobility was analysed. If the mobility was below a threshold value (the object has not moved more than a pixel (here 215-304 nm between two consecutive frames) the object was considered as immobile and therefore bound to the surface. The number of bound liposomes, i.e. the number of binding events, was recorded. The number of binding events for all wells were summed up before and after the addition of melagatran, respectively, to provide a cumulative number of binding events. This was done for each concentration of melagatran.

Figure 1:
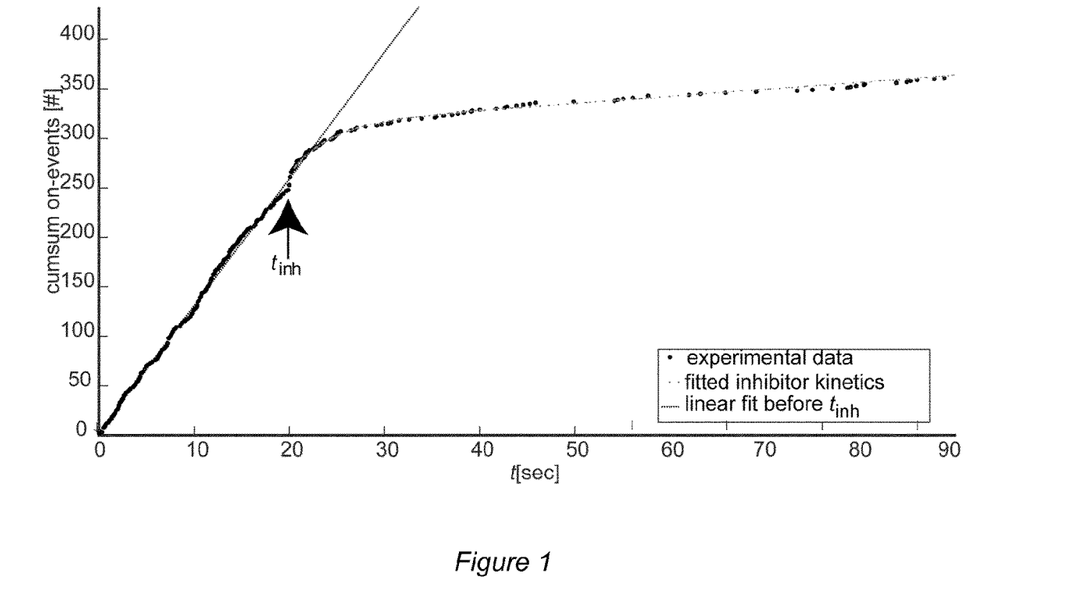
FIG. 1 is a graph showing the number of binding events as a function of time for liposome immobilized thrombin before and after the addition of melagatran.

The cumulative number of bound liposomes before and after the addition of melagatran was plotted versus time as shown in FIG. 1. In Figure A the concentration of melagatran was 200 nM and the concentration of thrombin was 15 pM. In FIG. 1 $t_{inh}$ is the time when the solution of melagatran was added to the solution containing the liposome immobilized thrombin, and cumsum on-events [#] is the number of recorded binding events.

Before the test compound melagatran was added the binding rate of liposomes to the surface was observed to be constant over time. Plotting the cumulative number of binding events versus time turned out to be a linear function where the slope equals the binding rate. During the injection and mixing of the test compound the binding rate to the surface was increased. After a short equilibration time the binding rate was normalized again. The data acquired during this mixing period was not used for analysis. The cumulative number of binding events was analysed as described herein and the observed binding rate constant $k_{obs}$ was extracted. Once the binding of melagatran to thrombin had reached its equilibrium the cumulative number of binding events versus time was increasing linearly again as shown in FIG. 1.

The ratio of the initial slope and the final slope was calculated. This was repeated three times for each concentration of melagatran. This ratio equals the fractional occupancy of thrombin by melagatran at the respective concentration. The equilibrium dissociation constant $K_d$ was then calculated from the equation below, wherein [melagatran]$_0$ is the concentration of the added melagatran.

$$\text{Fractional occupancy} = \frac{[melagatran]_0}{[melagatran]_0 + K_d}$$

Figure 2:
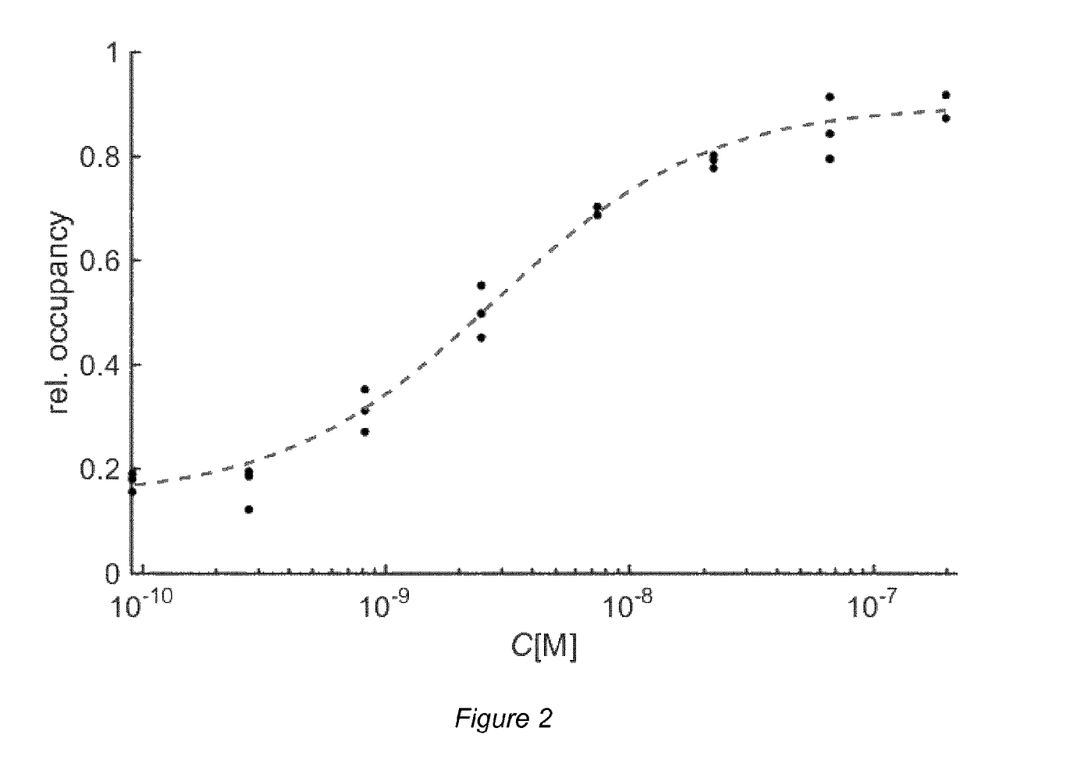
FIG. 2 is a graph showing a dose response curve for melagatran added to liposome immobilized thrombin.

The equilibrium dissociation constant $K_d$ was provided from a dose response curve wherein the fractional occupancy was plotted versus the added concentration of melagatran as shown in FIG. 2, which gave a $K_d$ value of about 3 nM.

Figure 3:
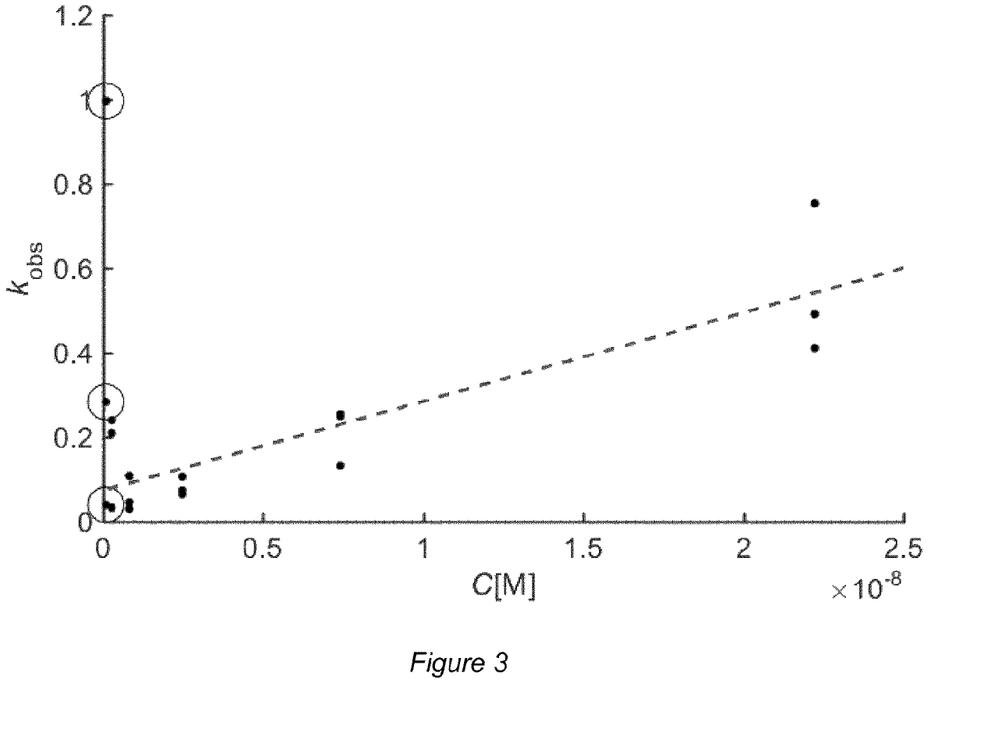
FIG. 3 is a graph showing the observed binding rate $k_{obs}$ as a function of the concentration of an added melagatran solution, and linear regression providing $k_{on}$ between melagatran and thrombin.

FIG. 3 shows the observed binding rate constant $k_{obs}$ plotted as a function of the concentration of the added test compound melagatran. Linear regression of the observed rate $k_{obs}$ versus the concentration of melagatran allowed for calculation of the association rate $k_{on}$ between melagatran and thrombin, which was found to be 21 µM$^{-1}$s$^{-1}$.

Since the equilibrium dissociation constant $K_d$ equals the dissociation rate $k_{off}$ divided by the association rate $k_{on}$, it was possible to calculate $k_{off}$ by multiplying the $k_{on}$ value of 21 µM$^{-1}$s$^{-1}$ with the $K_d$ value of 3 nM thereby providing a $k_{off}$ value of about 0.06 s$^{-1}$.

It was concluded that the method described herein allows for determining $k_{obs}$, $k_{on}$, $k_{off}$ and $K_d$ for a test compound and also the fractional occupancy of a receptor by the test compound. Thus, the method described herein allows for determining the interaction kinetics between a test compound and a receptor.

Example 2

In this example, the method steps described in Example 1 were performed in full in a single well, in each of two wells and in each of 100 wells. The thrombin concentration was 1 pM. The melagatran concentration was 7.4 nM.

Figure 4:
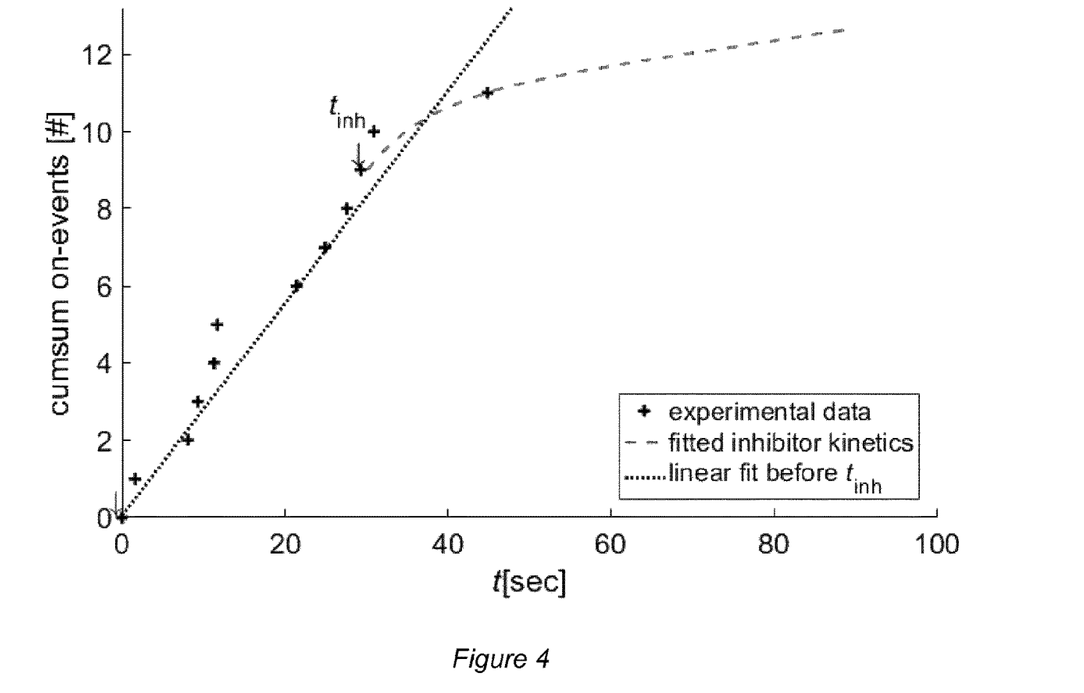
FIG. 4 is a graph showing the number of binding events in a single test well as a function of time for liposome immobilized thrombin before and after the addition of melagatran.
Figure 5:
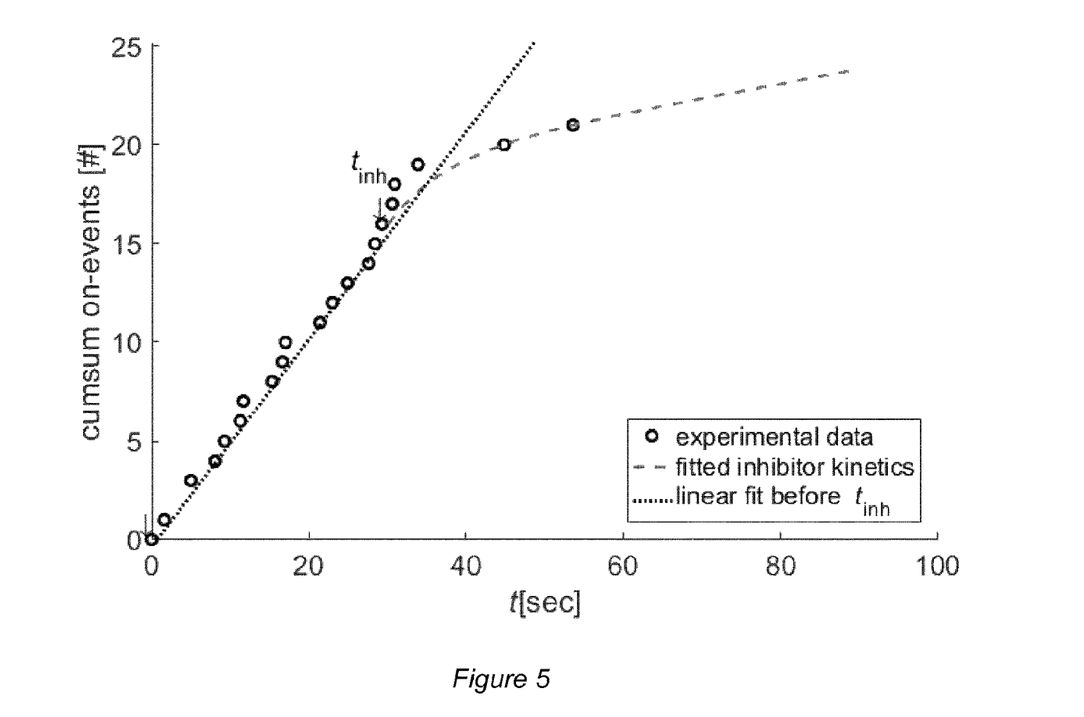
FIG. 5 is a graph showing the number of binding events in a two test wells as a function of time for liposome immobilized thrombin before and after the addition of melagatran.
Figure 6:
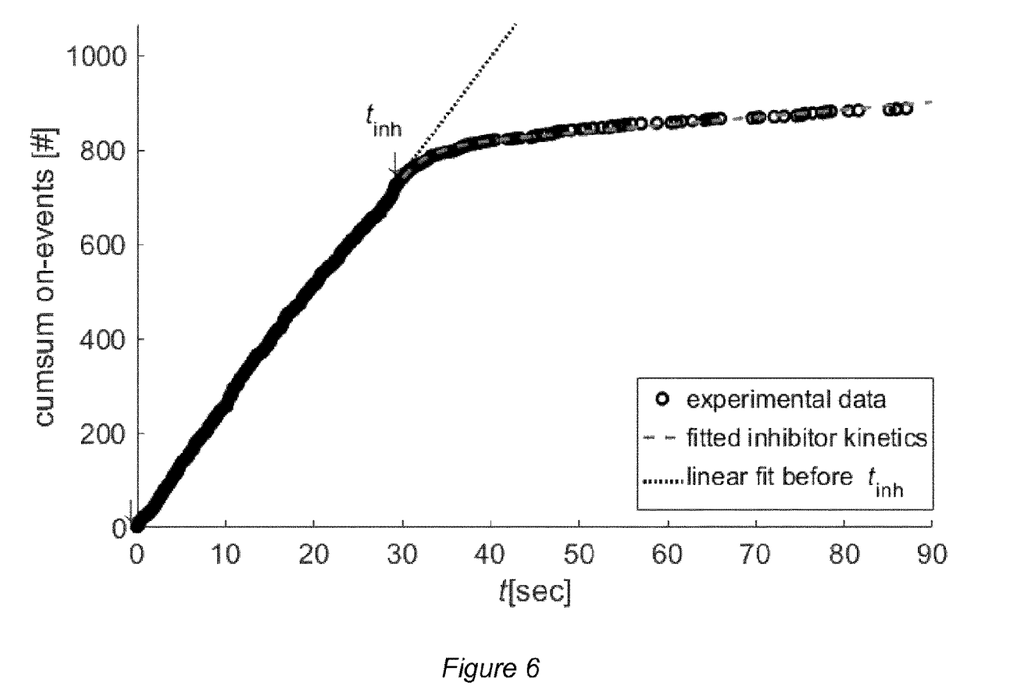
FIG. 6 is a graph showing the number of binding events in a one hundred test wells as a function of time for liposome immobilized thrombin before and after the addition of melagatran.

First, an experiment was performed in a single well. The number of binding events was plotted as a function of time as shown in FIG. 4. Due to the low number of binding events the observed rate constant $k_{obs}$ could not be reliably fitted. Therefore, the number of binding events were collected and summed up before and after the addition of melagatran, respectively, for two wells. The result is shown in FIG. 5, and it was found that $k_{obs}$ could be fitted to provide a $k_{obs}$ value of 0.43 sec$^{-1}$. A further experiment was performed in analogy with the two well experiment but instead of two wells one hundred wells were used. The result is shown in FIG. 6, and it was found that $k_{obs}$ could be fitted to provide a $k_{obs}$ value of 0.22 sec$^{-1}$. In FIGS. 4,5 and 6 $t_{inh}$ is the time when the solution of melagatran was added to the solution containing the liposome immobilized thrombin, and cumsum on-events [#] is the number of recorded binding events.

It was concluded that the sensitivity of the method described herein is enhanced by performing the method steps in a plurality of wells and summing up the recorded number of binding events of the wells before and after the addition of the test compound.

It was also concluded that the method described herein allows for reliable measurement of the observed rate constant $k_{obs}$ for a low receptor concentration such as a receptor concentration that is lower than the lowest concentration that corresponds to the LOD of ensemble averaging methods defining (i) how much material of the receptor that is needed to operate the assay and (ii) the tight binding regime with respect to high affinity test compounds.

REFERENCES

1. Geschwindner, S., Dekker, N., Horsefield, R., Tigerström, A., Johansson, P., Scott, C. W., and Albert, J. S. (2013). Development of a Plate-Based Optical Biosensor Fragment Screening Methodology to Identify Phosphodiesterase 10A Inhibitors. J. Med. Chem. 56, 3228-3234.
2. Motulsky, H. J., and Mahan, L. C. (1984). The kinetics of competitive radioligand binding predicted by the law of mass action. Mol. Pharmacol. 25, 1-9.
3. Schiele, F., Ayaz, P., and Fernández-Montalván, A. (2015). A universal homogeneous assay for high-throughput determination of binding kinetics. Anal. Biochem. 468, 42-49.
4. Gunnarsson, A., Snijder, A., Hicks, J., Gunnarsson, J., Höök, F., and Geschwindner, S. (2015). Drug discovery at the single molecule level: inhibition-in-solution assay of membrane-reconstituted β-secretase using single-molecule imaging. Anal. Chem. 87, 4100-4103.
5. Ola Wahlsten, Anders Gunnarsson, Lisa Simonsson Nyström, Hudson Pace, Stefan Geschwindner, and Fredrik Höök. Equilibrium-Fluctuation Analysis for Interaction Studies between Natural Ligands and Single G Protein-Coupled Receptors in Native Lipid Vesicles. *Langmuir*, 2015, 31 (39), pp 10774-10780.
6. Gunnarsson, A., Dexlin, L., Wallin, P.; Svedhem, S., Jönsson, P., Wingren, C. and Höök, F. (2011). J. Am. Chem. Soc. 133, 14852-14855.

The invention claimed is:
1. A method for determining the interaction between a first ligand and a receptor,
said method comprising a sequence of process steps:
a) providing a first solution free from the first ligand and comprising a concentration Ci of the receptor,
b) adding said first solution to a test well having a test well wall, thereby contacting said first solution with said test well wall being functionalized with a second ligand while recording the number of binding events between the receptor and the second ligand during a time interval t1, and
c) adding a test solution free from said receptor and comprising a concentration Cn of the first ligand to said test well having said test well wall containing the first solution after step b) thereby providing a second solution while continuing recording the number of binding events between the second ligand and the receptor in said second solution during a time interval t2, wherein an interaction between said first ligand and said receptor alters said number of binding events between said second ligand and said receptor, wherein the interaction between the first ligand and the receptor is determined based on data from the continuous recording of the number of binding events between the second ligand and the receptor, wherein the data from the continuous recording is obtained prior to an equilibrium binding being reached between the first ligand and the receptor.
2. The method according to claim 1, wherein the time interval $t_2$ is at least $1/k_{obs}$ of the binding reaction between the first ligand and the receptor.
3. The method according to claim 1, wherein the method further comprises the step of stopping the recording of the binding events between the second ligand and the receptor takes place after the first ligand and the receptor have reached equilibrium binding.
4. The method according to claim 1, wherein the method further comprises the step of stopping the recording of the binding events between the second ligand and the receptor takes place after the first ligand and the receptor have reached equilibrium binding.
5. The method according to claim 1, further comprising a step d):
d) determining the interaction between the first ligand and the receptor based on the binding events recorded in steps b) and c).
6. The method according to claim 1, wherein the sequence of process steps is performed in full in each of a plurality of test wells.
7. The method according to claim 1, wherein the sequence of process steps is performed for a number of different concentrations Cn of the first ligand in said test solution.
8. The method according to claim 1 further comprising a step e):
e) repeating step c) at an increasing concentration $C_n$ of the first ligand in said test solution.
9. The method according to claim 1, wherein
the receptor is combined with a vehicle, thereby providing an immobilized receptor.
10. The method according to claim 9, wherein the vehicle comprises a fluorophore.
11. The method according to claim 1, wherein the first ligand and the second ligand are identical.
12. The method according to claim 1, wherein the first ligand and the second ligand are different.
13. The method according to claim 1, wherein:
the receptor is a pharmaceutical drug receptor, and/or
the first ligand and/or the second ligand is/are a pharmaceutical drug.
14. The method according to claim 1, wherein step b) and/or step c) comprise(s) use of a microscope.
15. The method according to claim 1, which comprises determination for the first ligand at least one of the follow- ing: an observed rate constant $k_{obs}$, an association constant $k_{on}$, a dissociation constant $k_{off}$, an equilibrium dissociation constant $K_d$, a fractional occupancy.

16. The method according to claim 6, wherein the plurality of test wells form part of a sample holder assembly.

17. The method according to claim 16, wherein the sample holder assembly comprises or consists of a microtiter plate.

18. The method according to claim 16, wherein the sample holder assembly is configured to be used in combination with Total Internal Reflection Fluorescence (TIRF) microscopy, and comprises:
- a sample holder plate comprising a plurality of bottomless test wells,
- a bottom plate attached to said sample holder plate by means of a material thereby forming a well bottom wall of said plurality of test wells, said material having a refractive index ($N_a$) that is lower than a refractive index ($N_g$) of said bottom plate.

19. The method according to claim 18, wherein said material is UV curable and/or resistant to buffer solutions.

20. The method according to claim 18, wherein said material is an adhesive.

21. The method according to claim 16, wherein the sample holder assembly is combined with a TIRF source configured to provide a light beam into the well bottom wall such that the light beam propagates throughout the entire well bottom wall thereby creating an evanescent field in the plurality of wells.

22. The method according to claim 9, wherein the vehicle comprises a liposome, a dendrimer, a dendrone, a complexed lanthanide, a quantum dot, a nanodiamond, or a lipid disc.

* * * * *